(12) United States Patent
Fleming et al.

(10) Patent No.: US 6,208,256 B1
(45) Date of Patent: Mar. 27, 2001

(54) AUTOMOBILE CARBON MONOXIDE DETECTION AND CONTROL DEVICE

(76) Inventors: Raymond Fleming; Allison A. Fleming, both of 1413 Summit Ave., Monessen, PA (US) 15062

( * ) Notice: Subject to any disclaimer, the term of this patent is extended or adjusted under 35 U.S.C. 154(b) by 0 days.

(21) Appl. No.: 09/426,621

(22) Filed: Oct. 26, 1999

(51) Int. Cl.[7] .................................................. G08B 17/10
(52) U.S. Cl. ....................... 340/632; 340/438; 180/271
(58) Field of Search .................... 340/430, 438, 340/632, 539; 180/271, 273, 279

(56) References Cited

U.S. PATENT DOCUMENTS

| | | | |
|---|---|---|---|
| 4,221,206 | * | 9/1980 | Haas . |
| 4,924,095 | * | 5/1990 | Swanson, Jr. . |
| 5,199,397 | * | 4/1993 | Shelef et al. . |
| 5,333,703 | * | 8/1994 | James et al. . |
| 5,371,367 | * | 12/1994 | DiDomenico et al. . |
| 5,418,366 | * | 5/1995 | Rubin et al. . |
| 5,591,975 | * | 1/1997 | Jack et al. . |
| 5,739,756 | * | 4/1998 | Margulies .............................. 340/632 |
| 5,764,150 | * | 6/1998 | Fleury et al. ......................... 340/632 |
| 5,831,267 | * | 11/1998 | Jack et al. . |
| 6,057,755 | * | 5/2000 | Phillips ................................. 340/438 |
| 6,072,398 | * | 6/2000 | Hayes et al. .......................... 340/632 |

* cited by examiner

*Primary Examiner*—Daniel J. Wu
(74) *Attorney, Agent, or Firm*—John D. Gugliotta

(57) ABSTRACT

An automobile carbon monoxide detection and control device is provide that interfaces with various elements of a vehicle to allow for shutoff or control of a vehicle's motor or windows as a function of carbon monoxide level.

4 Claims, 5 Drawing Sheets

AUTOMOBILE CARBON MONOXIDE DETECTION AND CONTROL DEVICE

RELATED APPLICATIONS

The present invention was first described in Disclosure Document Number 456,988 filed on Jun. 1, 1999. There are no previously filed, nor currently any co-pending applications, anywhere in the world.

BACKGROUND OF THE INVENTION

1. Field of the Invention

The present invention relates generally to carbon monoxide sensing devices and, more particularly, to carbon monoxide sensing system for motor vehicles

2. Description of the Related Art

A search of the prior art did not disclose any patents that read directly on the claims of the instant invention; however, the following patents disclose a method and apparatus for remote measurement of exhaust gas:

U.S. Pat. No. 5,831,267* issued in the name of Jack et al.;

U.S. Pat. No. 5,591,975* issued in the name of Jack et al.;

U.S. Pat. No. 5,418,366* issued in the name of Jack et al.;

U.S. Pat. No. 5,371,367* issued in the name of DiDomenico et al; and

U.S. Pat. No. 4,924,095* issued in the name of Swanson, Jr.

Also, U.S. Pat. No. 5,764,150* issued in the name of Fleury et al. describes a carbon monoxide sensor and processor with an audible and visual alarm.

Further, U.S. Pat. No. 5,739,756* issued in the name of Margulies discloses a carbon monoxide detection system for motor vehicles.

Also, the following patents describe a carbon monoxide detector and deactivating mechanism for engines:

U.S. Pat. No. 5,333,703** issued in the name of James et al.;

U.S. Pat. No. 5,199,397** issued in the name of Shelef et al.; and

U.S. Pat. No. 4,221,206** issued in the name of Haas.

Consequently, a need has therefore been felt for an improved but less complex mechanism that allows for the use of vehicle carbon monoxide sensors that interlock with various conventional elements of the vehicle.

SUMMARY OF THE INVENTION

It is therefore an object of the present invention to provide an improved carbon monoxide sensing system.

It is a feature of the present invention to provide an improved carbon monoxide sensing system for use with vehicles.

Briefly describe according to one preferred embodiment, the present invention operates in the same manner similarly as conventional carbon monoxide sensors found inside of homes. A dash mounted display continually informs the driver of the status of the system, current carbon monoxide level and the ability to test the system. The ability to always see the current level of carbon monoxide is important during winter driving, where long periods of idling with the windows closed up may result in elevated levels of carbon monoxide, that though not deadly, certainly impact the occupant's health. An interlock to the ignition system of the vehicle allows for the automatic shutdown of the engine upon sensing dangerous levels of carbon monoxide, as well as the inability to start the engine until the carbon monoxide levels have returned to a safe level.

One advantage of the present invention will allow for preventing accidental and intentional deaths from carbon monoxide as well as provides for the increased health of motor vehicle occupants by making them aware of carbon monoxide levels, thus allowing them time to take steps to reduce them.

Further, an engine interlock feature will allow for automatically shutting the engine on dangerously high carbon monoxide levels, and preventing vehicles from restarting until levels have receded to safe level.

DESCRIPTIVE KEY

| | | | |
|---|---|---|---|
| 10 | automobile carbon monoxide detection and control device | 115 | antenna |
| | | 120 | first wireless link |
| 15 | automobile dashboard | 125 | radio reception tower |
| 20 | automobile | 130 | central monitoring station |
| 25 | carbon monoxide sensors | 135 | land based communication path |
| 30 | control panel | | |
| 35 | audible alarm horn | 140 | emergency response vehicle |
| 40 | numeric readout | 145 | public service frequency |
| 45 | motion sensor | 150 | second wireless link |
| 50 | power indicator light | 155 | satellite |
| 55 | help summoned indicator light | 160 | third wireless link |
| 60 | power window activation indicator light | 165 | first functional block |
| | | 170 | first operational block |
| 65 | warning indicator light | 175 | second functional block |
| 70 | alarm indicator light | 180 | second operational block |
| 75 | test pushbutton | 185 | third functional block |
| 80 | motor vehicle electrical power source | 190 | fourth functional block |
| | | 195 | third operational block |
| 85 | ignition switch | 200 | calculation block |
| 90 | ground connection | 205 | fifth functional block |
| 95 | engine shutdown relay | 210 | fourth operational block |
| 100 | power window electric motors | 215 | sixth functional block |
| 105 | speed detection sensor | 220 | fifth operational block |
| 110 | wireless transmitter | 225 | seventh functional block |

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

DESCRIPTION OF THE PREFERRED EMBODIMENTS

The best mode for carrying out the invention is presented in terms of its preferred embodiment, herein depicted within the FIGS. 1 through 5.

1. Detailed Description of the Figures

Figure 1:
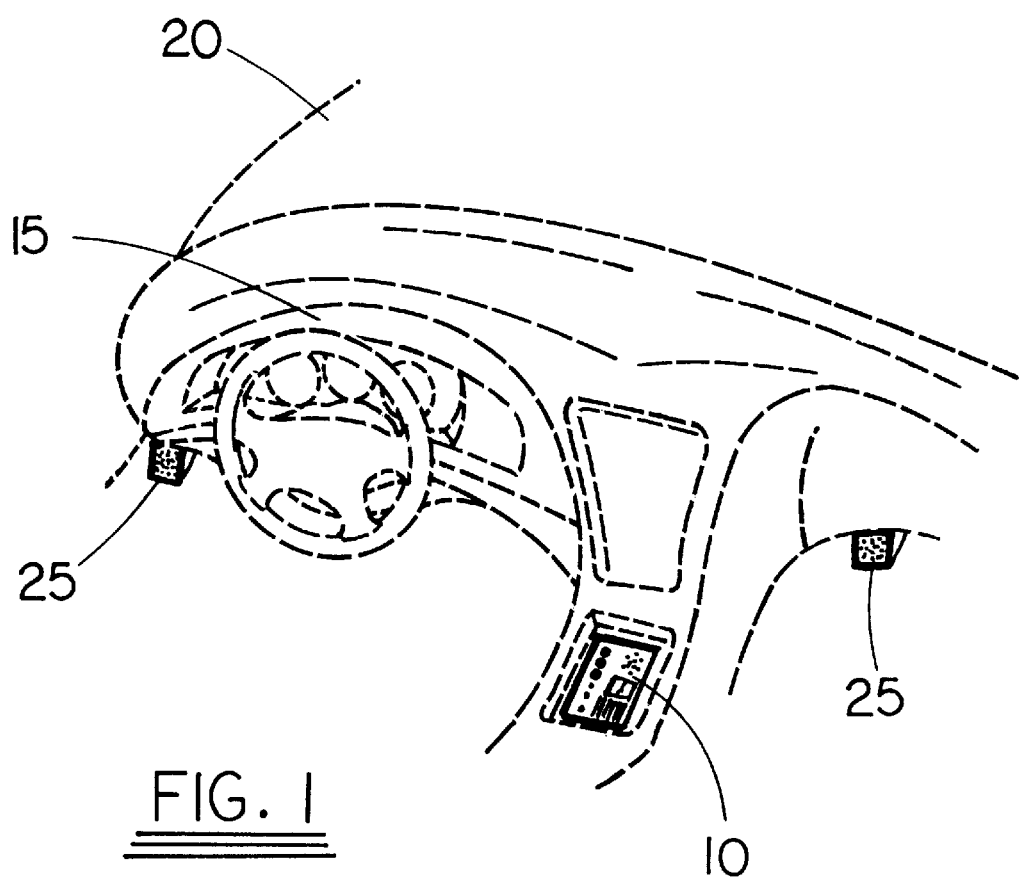
FIG. 1 is a perspective view of the automobile carbon monoxide detection and control device 10 shown in an installed state on a motor vehicle dashboard according to a preferred embodiment of the present invention.

Referring now to FIG. 1, an automobile carbon monoxide detection and control device 10 is shown in an installed state upon an automobile dashboard 15 of an automobile 20. The automobile dashboard 15 is located in close proximity to the driver of the automobile 20 so that it may be easily viewed. A pair of carbon monoxide sensors 25 are located directly beneath the automobile dashboard 15, one per side as shown. It is envisioned that multiple sensors will allow for alarm verification and the prevention of false or inaccurate readings by the comparison of level readings from each of the sensor. While two carbon monoxide sensors 25 are disclosed in FIG. 1, it is for illustrative purposes only and the quantity is not intended to be a limiting factor.

Figure 2:
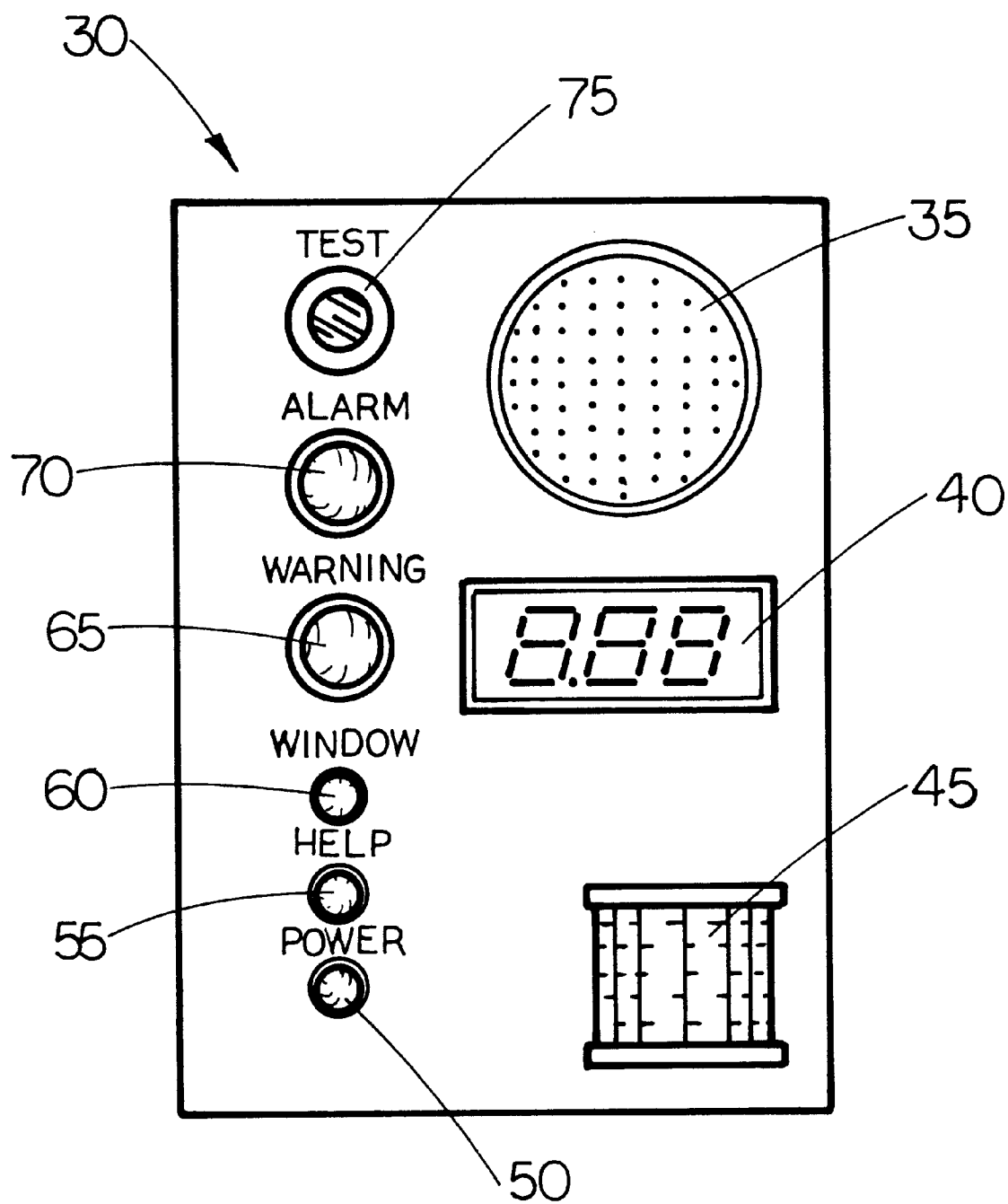
FIG. 2 is a front view of the control panel associated with the automobile carbon monoxide detection and control device 10.

Referring next to FIG. 2, a front view of the control panel 30 is depicted. In the upper right-hand corner of the control panel 30 is an audible alarm horn 35. The audible alarm horn 35 provides a two-stage audible warning indication of the level of carbon monoxide as detected by the carbon monoxide sensors 25 (not shown in this FIG.) The audio level of the audible alarm horn 35 is such that it will be readily heard by all occupants of the automobile 20 (not shown in this FIG.) Located below the audible alarm horn 35 is a numeric readout 40. The numeric readout 40 continuously displays the relative concentration of carbon monoxide in a parts per million format. With the use of the numeric readout 40 the occupants can determine the relative severity of the carbon monoxide levels and the rate at which they are rising and/or falling. Located at the lower right-hand corner of the control panel 30 is a motion sensor 45. The motion sensor 45 is envisioned to be of the infrared detection type, though it can be seen by those familiar in the art that other types such as ultrasonic or microwave could also be used with equal effectiveness. The motion sensor 45 is used to determine if someone is inside the passenger compartment of a motor vehicle and is used to initiate additional actions as will be described herein below. Located in the lower left hand corner of the control panel 30 is a power indicator light 50 which functions in a customary manner and is envisioned to be active whenever the ignition key of the vehicle is in any position other than the off position. Located above the power indicator light 50 is a help summoned indicator light 55 which indicates that a request for help has been dispatched through a cellular phone link, a satellite link or radio link. The procedure for requesting outside assistance will be described in greater detail herein below. Located above the help summoned indicator light 55 is a power window activation indicator light 60. The power window activation indicator light 60 is used to signify that certain conditions have been achieved and the windows of the automobile 20 (not shown in this FIG.) have been lowered. Above the power window activation indicator light 60 is a warning indicator light 65 which is used to indicate that carbon monoxide levels have reached a level that, while not life threatening, are of a level that close monitoring is required. Directly above the warning indicator light 65 is an alarm indicator light 70 which indicates life threatening levels of carbon monoxide. The levels at which the warning indicator light 65 and the alarm indicator light 70 activate are beyond the scope of this patent and are continually being refined and tweaked by research and testing laboratories. It is envisioned that the warning and alarm levels would be internally adjustable by qualified technicians. The warning indicator light 65 and the alarm indicator light 70 work in conjunction with the audible alarm horn 35 to provide both audible and visual indication of high levels of carbon monoxide. This is envisioned to be advantageous to those drivers who may be audibly impaired. Finally, located in the upper left hand corner of the control panel 30 is a test pushbutton 75, which is used to test all sensing and alarm features as described in this FIG.

Figure 3:
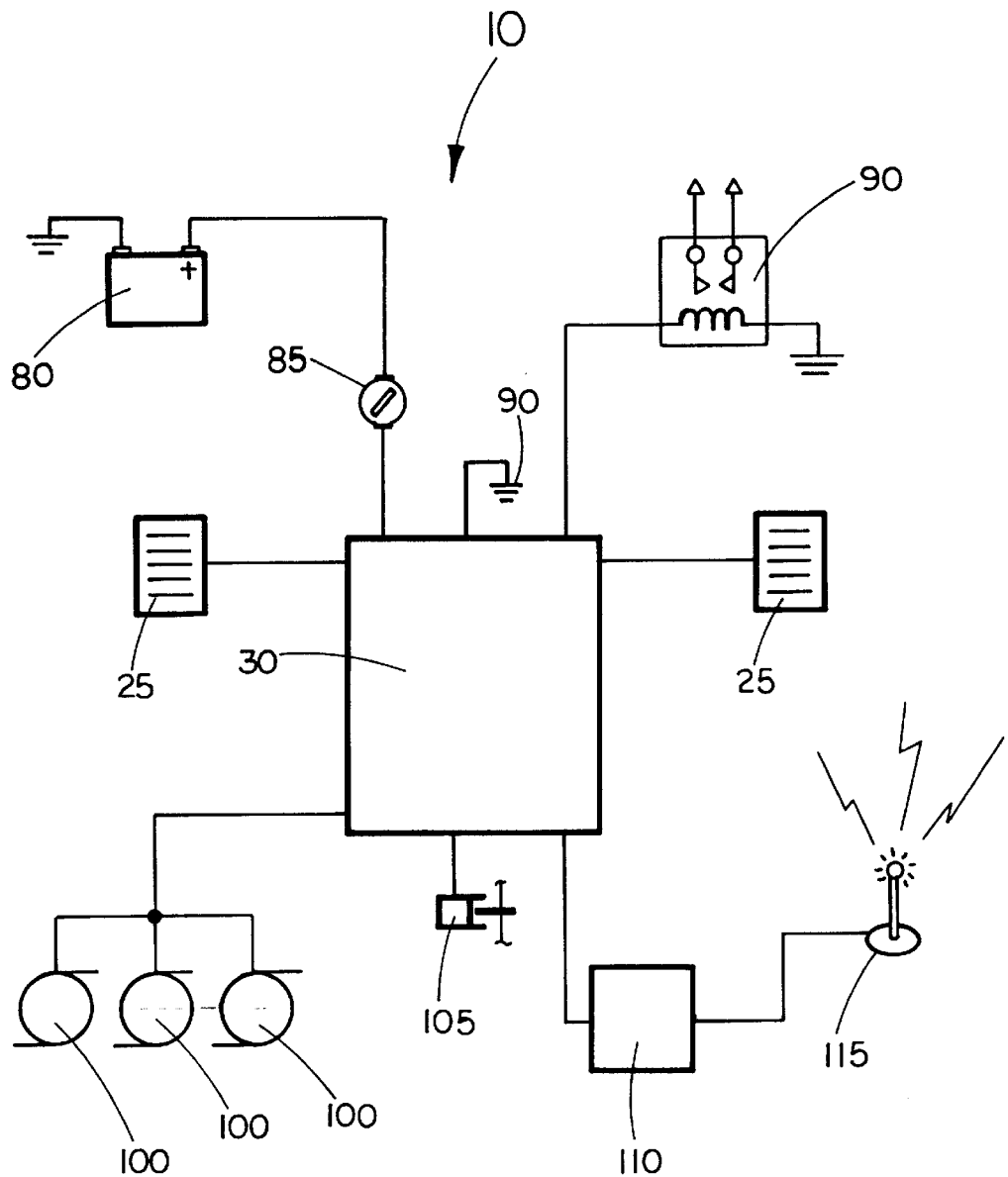
FIG. 3 is an electrical block diagram of the present invention depicting major electrical components.

Referring now to FIG. 3, an electrical block diagram depicting the major electrical interconnections of the automobile carbon monoxide detection and control device 10 is shown. A power connection to the control panel 30 is made to a motor vehicle electrical power source 80, such as a battery, through an ignition switch 85. The ignition switch 85 provides power to the control panel 30 at all times except when the automobile 20 (not shown in this FIG.) shown in this FIG.) is in the "OFF" position. The return power path is provided by a ground connection 90. The ground connection 90 serves as a return path for all external devices as well. Both carbon monoxide sensors 25 (as shown in FIG. 1) are wired into the control panel 30 as shown. There is also a connection from the control panel 30 to an engine shutdown relay 95. The engine shutdown relay 95 allows the automobile carbon monoxide detection and control device 10 to shut down the automobile 20 (not shown in this FIG.) should dangerous levels of carbon monoxide persist. To further combat high levels of carbon monoxide, a connection is made from the control panel 30 to a plurality of power window electric motors 100. This connection allows the automobile carbon monoxide detection and control device 10 to automatically lower the power windows (if so equipped) of the automobile 20 (not shown in this FIG.) However, this action will only occur if the vehicle is moving above a certain speed. This is due to the fact that carbon monoxide levels may actually rise inside the automobile 20 (not shown in this FIG.) should the windows be lowered while the vehicle is at a standstill or while moving slowly. This detection of the minimal speed is performed by a speed detection sensor 105 which is also connected to the control panel 30. The final connection from the control panel 30 is made to a wireless transmitter 110 which transmits a request for help via the use of an antenna 115. It is envisioned that the wireless transmitter 110 would utilize conventional cellular telephone protocols, but other means such as satellite, general radio frequencies, amateur radio frequencies and the like could also be utilized with equal effectiveness.

Figure 4:
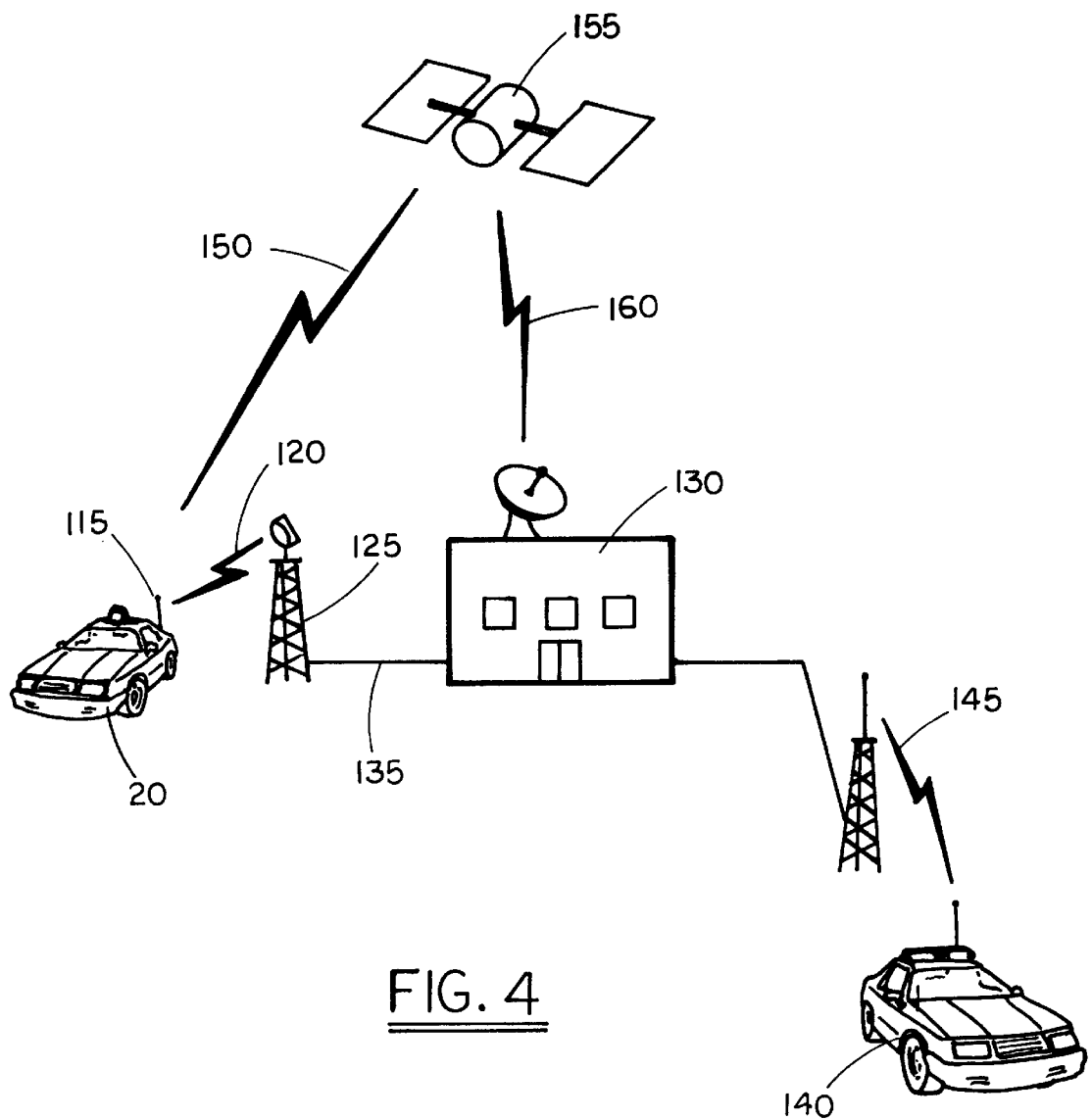
FIG. 4 is a pictorial representation of the wireless radio frequency link as used with the automobile carbon monoxide detection and control device 10.

Referring next to FIG. 4, a pictorial representation of the wireless radio link between the various communication systems is depicted. In the event of an alarm condition, a first wireless link 120 leaves from the antenna 115 as provided on the automobile 20. The first wireless link 120 is envisioned to be of the cellular telephone link, possibly of the variety of the emergency rescue systems commonly found on late model, higher end automobiles. The first wireless link 120 is received by a radio reception tower 125 nearest the vicinity of the automobile 20. The signal then continues to a central monitoring station 130 via a land-based communication path 135. The central monitoring station 130 then alerts an emergency response vehicle 140 via a public service frequency 145. It is also envisioned that satellite-based communication could occur through the use of a second wireless link 150 to a satellite 155. The satellite 155 will then communicate to a central monitoring station 130 through the use of a third wireless link 160. The use of the satellite-based system will allow continuous coverage all over the earth, which would be more advantageous than cellular-based links which are not continuous. This FIG. is intended to depict how the automobile carbon monoxide detection and control device 10 would alert authorities via a wireless link and is not intended to eliminate the possibility of other wireless connection means or other means that may be developed in the future.

Figure 5:
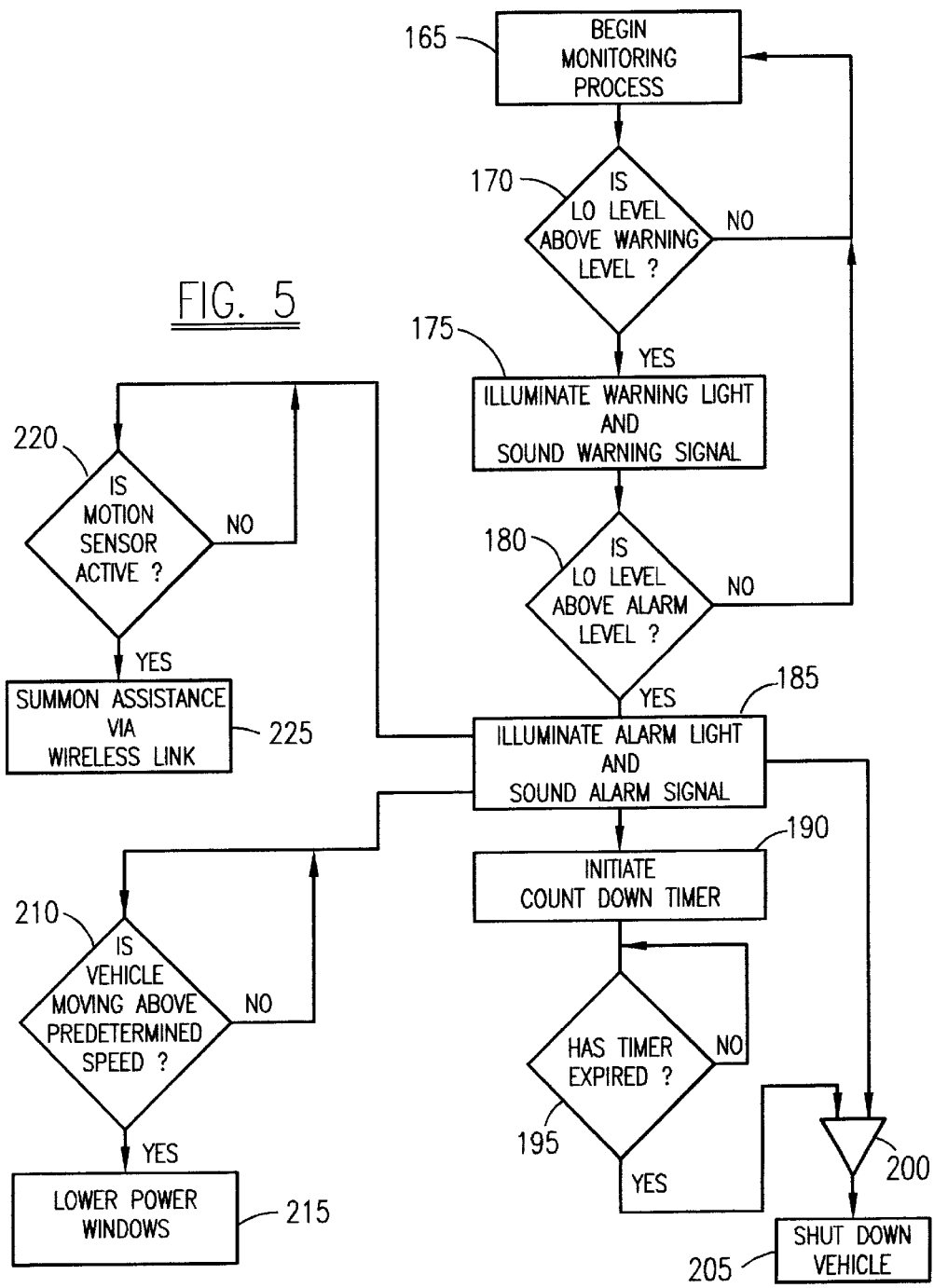
FIG. 5 is a flow diagram depicting the internal logic and control of the automobile carbon monoxide detection and control device 10.

Referring finally to FIG. 5, a flow diagram depicting the internal logic and control functions of the automobile carbon monoxide detection and control device 10 is depicted. Whenever power is applied to the automobile carbon monoxide detection and control device 10, the logic functions will begin at a first functional block 165 and follow through to a first operational block 170. A negative response to the first operational block 170 will return operation to the first functional block 165, which depicts the normal operating sequence with normal levels of carbon monoxide. However, a positive response will cause the to operation of the warning indicator light 65 (not shown in this FIG.) and the warning level of the audible alarm horn 35 (not shown in this FIG.) by the use of the second functional block 175. The detection and warning sequence then continues with a second operational block 180 that monitors for dangerous levels of carbon monoxide. A negative response to this returns control to the first functional block 165, where the process begins anew. A positive response however, dictates the beginning of many operations that begins with a third functional block 185. The third functional block 185 causes the indication of the alarm indicator light 70 (not shown in this FIG.) and the warning level of the audible alarm horn 35 (not shown in this FIG.) The sequence then continues with the initialization of a countdown timer as depicted by a fourth functional block 190. The progress and completion of the countdown timer are provided by a third operational block 195 and its associated negative response. Upon the completion of the third operational block 195 a positive response and the positive response of the third functional block 185 are summed together at a calculation block 200. At this point, the vehicle is shutdown at a fifth functional block 205. In this manner, after the alarm signal is first received, the operator of the motor vehicle will have a predetermined time period in which to shut down the vehicle before the automobile carbon monoxide detection and control device 10 (not shown in this FIG.) will shut the vehicle down on its own. Also at the point of the third functional block 185, a check to make sure the vehicle is above a certain speed is made a fourth operational block 210. A negative response allows the loop to continue and a positive response causes the power windows of the automobile 20 (not shown in this FIG.) to open at a sixth functional block 215. A similar type loop checks to see if anyone is present inside the passenger compartment of the automobile 20 (not shown in this FIG.) at a fifth operational block 220 forces the request for emergency assistance via the wireless link at a seventh Functional block 225.

It is envisioned that other styles and configurations of the present invention can be easily incorporated into the teachings of the present invention, and only one particular configuration shall be shown and described for purposes of clarity and disclosure and not by way of limitation of scope.

2. Operation of the Preferred Embodiment

The preferred embodiment of the present invention can be used by the common user in a simple and effortless manner. The operation of the automobile carbon monoxide detection and control device 10 is best described in conjunction with FIG. 1, FIG. 2, FIG. 3, FIG. 4 and FIG. 5.

It is envisioned that the automobile carbon monoxide detection and control device 10 would be available as standard or optional equipment on new motor vehicles as a factory installed component. It is also envisioned that the automobile carbon monoxide detection and control device 10 could be made available in kit format for aftermarket use on existing vehicles. Once installed, the automobile carbon monoxide detection and control device 10 operates in a transparent manner that is simple and effortless to the common user. The automobile carbon monoxide detection and control device 10 is activated whenever the vehicle is operational, thus ensuring that its safety features will be available at all times even to those users who are not aware of its presence.

Once activated through the ignition switch 85 the automobile carbon monoxide detection and control device 10 simply monitors for dangerous levels of carbon monoxide in a manner similar to that used by common detectors used inside living quarters. A warning level is provided at minimal concentration of carbon monoxide. The operator of the automobile 20 will become aware of this condition through the audible alarm horn 35 and the warning indicator light 65. At this point the user is responsible for reducing the level of carbon monoxide through various actions such as manually opening windows, shutting the vehicle down, increasing velocity or the like. Upon the continual increase of carbon monoxide levels, the automobile carbon monoxide detection and control device will activate the alarm indicator light 70 and the alarm signal of audible alarm horn 35. A timer is then initialized that will shut the vehicle down after a predetermined time limit, thus ensuring the decrease of carbon monoxide levels. If the automobile 20 is moving, the power windows will be lowered so that fresh air may, enter the passenger compartment and a corresponding decrease in carbon monoxide levels. Finally, if movement is detected inside the vehicle with high levels of carbon monoxide concentrations, the automobile carbon monoxide detection and control device 10 will request outside help via emergency personnel via a wireless cellular link, a satellite link or the like.

The foregoing description is included to illustrate the operation of the preferred embodiment and is not meant to limit the scope of the invention. The scope of the invention is to be limited only by the following claims.

What is claimed is:

1. An automobile carbon monoxide detection and control device comprising:

at least one carbon monoxide sensors, each said sensor located directly beneath the automobile dashboard;

an audible alarm horn in communication with said sensors for providing a two-stage audible warning indication of the level of carbon monoxide as detected by said carbon monoxide sensors;

a numeric readout in communication with said sensors for providing numeric readout for continuously displaying the relative concentration of carbon monoxide; and motion sensing means for determining if someone is inside the passenger compartment of a motor vehicle, said motion sensing means further for interlocking, controlling, and communicating with said audible alarm horn and said numeric readout.

2. The automobile carbon monoxide detection and control device of claim 1, further comprising:

help summoning means for communicating the activation of said audible alarm horn to a remote locations.

3. The automobile carbon monoxide detection and control device of claim 2, wherein said help summoning means utilizes a communication method selected from the group comprising a cellular phone link, a satellite link, and a radio link.

4. The automobile carbon monoxide detection and control device of claim 1, further comprising power window activation means, and wherein when certain conditions have been achieved and the windows of the automobile are automatically lowered.

* * * * *